March 16, 1965 F. A. HENDERICKX Plant Pat. 2,487
TAXUS PLANT
Filed Sept. 19, 1963 2 Sheets-Sheet 1
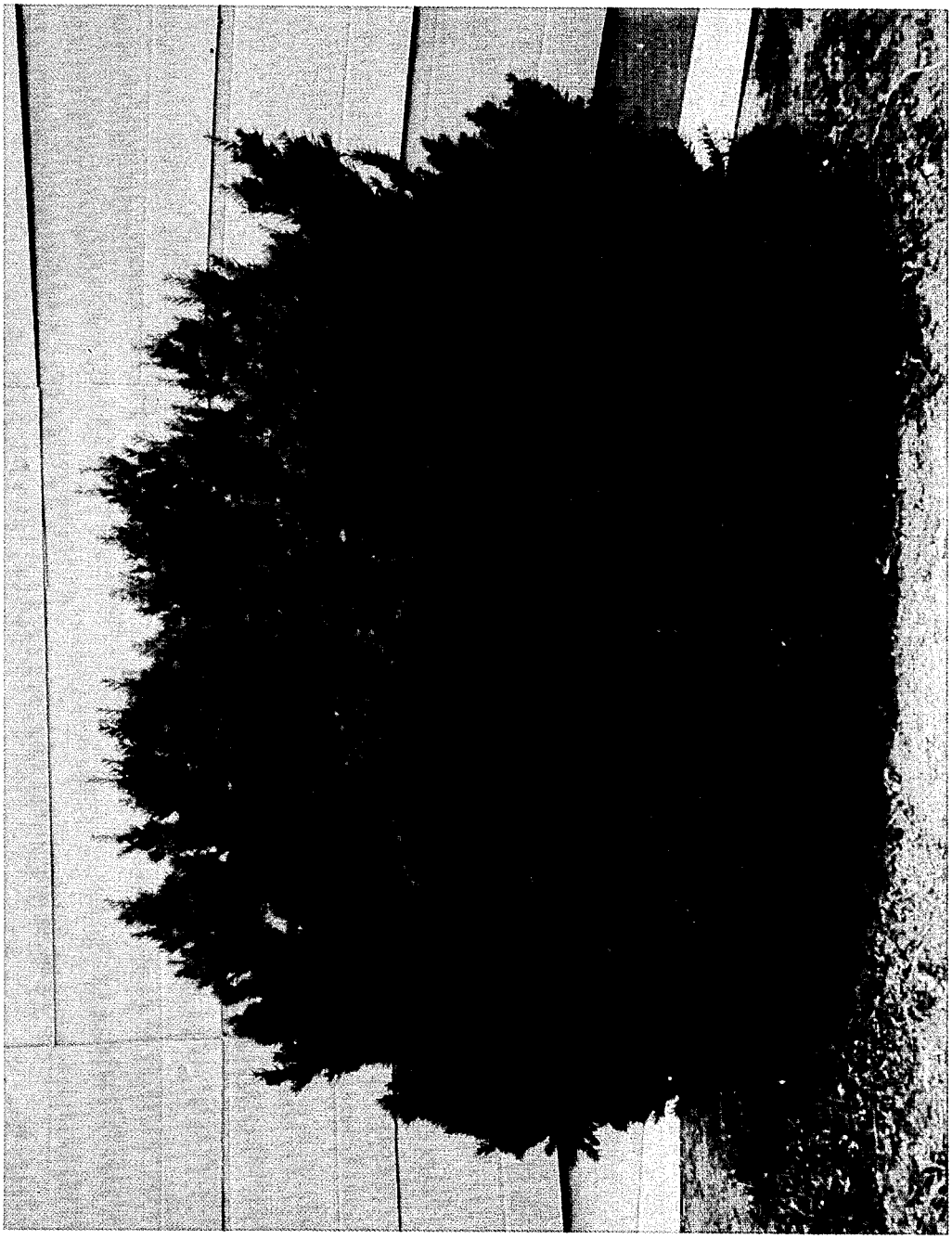
Inventor.
F. A. Henderickx
By: Robb & Robb
Attorneys.

March 16, 1965 F. A. HENDERICKX Plant Pat. 2,487
TAXUS PLANT
Filed Sept. 19, 1963 2 Sheets-Sheet 2
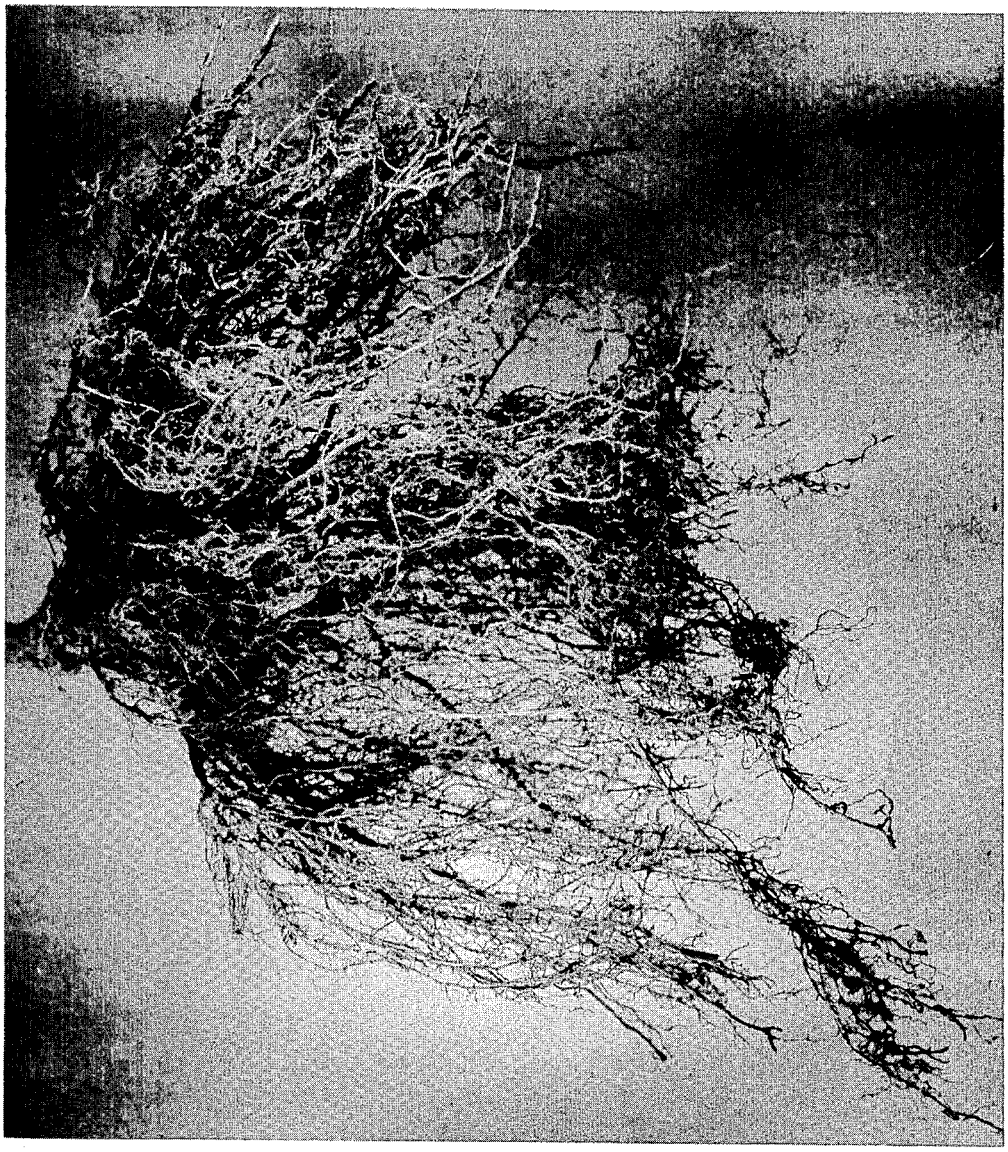
Inventor.
Fritz A. Henderickx
By: Robert Robb
Attorneys.

United States Patent Office

Plant Pat. 2,487
Patented Mar. 16, 1965

2,487
TAXUS PLANT

Fritz A. Henderickx, East Rutherford, N.J., assignor to Bobbink Nurseries, Inc., Freehold, N.J., a corporation of New Jersey Filed Sept. 19, 1963, Ser. No. 310,181
1 Claim. (Cl. Plt.—50)

The present invention relates to a new and distinct variety af Taxus plant (commonly known as yew), which was originated by me by crossing an unnamed and unpatented seedling derived from a cross of unnamed and unpatented varieties of the *T. media* and *T. cuspidata* types, with another unnamed and unpatented variety of unidentified parentage.

The primary objective of this breeding was to produce a new and improved ornamental type of Taxus of outstanding color and hardiness. This objective was fully achieved, along with other desirable features, as evidenced by the following unique combination of characters which are outstanding in the new variety and which distinguish it from its parents, as well as from all other varieties of which I am aware:

(1) A generally globular form, with a naturally compact growth which is taller in the center than the outer growth so as to achieve a globular form with little or no trimming, while at the same time having a sturdy branch structure;

(2) a fine, fibrous root system which enables easy transplanting and promotes vigorous and sturdy growth;

(3) Dark green foliage which remains substantially uniform in color throughout the entire year;

(4) A whorled arrangement of the needles which are narrower and shorter than those of the variety botanically known as *T. cuspidata,* with consequent attainment of a very compact plant;

(5) An excellent ability to propagate readily; and (6) Good hardiness, as evidenced by having withstood temperatures as low as 12 degrees below zero at East Rutherford, New Jersey, without material damage or injury.

Asexual reproduction of my new variety by cuttings, as performed by me at East Rutherford, New Jersey, shows that the foregoing characteristics and distinctions come true to form and are established and transmitted through succeeding propagations.

The accompanying drawings show a typical specimen plant of my new Taxus variety, as depicted in color as nearly true as it is reasonably possible to make the same, and also a typical speciment of the root system, as depicted in black and white to illustrate the fine and fibrous growth thereof.

The following is a detailed description of my new variety, with color terminology in accordance with the Nickerson Color Fan, as published by Munsell Color Company, Inc., of Baltimore, Maryland, except where general color terms of ordinary dictionary significance are obvious:

Type: Bush; much branched; semi-upright; compact.

Parentage:

*Seed parent.*—An unnamed seedling of *T. media*×*T. cuspidata* types.

*Pollen parent.*—An unnamed seedling of unidentified parentage.

Propagation: Holds its distinguishing characteristics excellently through succeeding propagations by cuttings.

Locality where grown and observed: East Rutherford, New Jersey.

Habit of growth: Medium vigorous; growth rate about 7 inches to 10 inches per year; average height about 4½ feet to 5 feet; average width about 5 feet to 5½ feet; compact; top center of plant somewhat taller than outer branches with consequent attainment of a natural substantially globular form.

Form: Bush; much-branched; semi-upright; compact.

Branches: Numerous; sturdy.

Root system: Fine; fibrous.

Foliage: Needles are whorled around the stem, and are narrower and shorter than those of *T. cuspidata,* thus achieving a very compact plant habit.

*Size.*—Medium, from about ⅛ inch to ¼ inch long, and about 3/16 inch wide.

*Quantity.*—Abundant.

*Color.*—New foliage: upper side—Moderate Yellow Green, Plate 5GY 5/6; under side—Moderate Yellow Green, Plate 2.5GY 5/5. Old foliage: upper side—Grayish Olive Green, Plate 7.5GY 3/2; under side—Moderate Olive Green, Plate 7.5GY 4/4.

*Texture.*—Upper side—glossy; smooth. Under side—smooth.

Flower: Staminate.

Fruit: Has never been known to bear fruit.

Hardiness: Good; has withstood winter temperature as low as 12 degrees below zero without material damage or injury, and has never been hurt by late frosts to which many other Taxus varieties have been susceptible.

I claim:

A new and distinct variety of Taxus plant, substantially as herein shown and described, characterized particularly as to novelty by the unique combination of a naturally globular form, a fine and fibrous root system, a distinctive and attractive dark green foliage and retention of the color throughout the entire year, relatively narrow and short needles which are whorled around the stem, with consequent attainment of a dense and compact habit of plant growth, an excellent ability to propagate readily, and good hardiness to low temperatures and early frost.

No references cited.

T. GRAHAM CRAVER, *Primary Examiner.*

ABRAHAM G. STONE, *Examiner.*